(12) United States Patent
Lim et al.

(10) Patent No.: US 7,081,560 B1
(45) Date of Patent: ***Jul. 25, 2006

(54) ABSORBENT ARTICLES UTILIZING BREATHABLE COMPOSITE SHEET

(75) Inventors: Hyun Sung Lim, Midlothian, VA (US); George Joseph Ostapchenko, Salem, SC (US)

(73) Assignee: The Procter & Gamble Company, Cincinnati, OH (US)

( * ) Notice: Subject to any disclaimer, the term of this patent is extended or adjusted under 35 U.S.C. 154(b) by 479 days.

This patent is subject to a terminal disclaimer.

(21) Appl. No.: 09/980,330

(22) PCT Filed: Jun. 2, 2000

(86) PCT No.: PCT/US00/15199

§ 371 (c)(1),
(2), (4) Date: Mar. 27, 2002

(87) PCT Pub. No.: WO00/72794

PCT Pub. Date: Dec. 7, 2000

Related U.S. Application Data

(60) Provisional application No. 60/137,198, filed on Jun. 2, 1999.

(51) Int. Cl.
*A61F 13/15* (2006.01)

(52) U.S. Cl. ..................... 604/367; 604/367

(58) Field of Classification Search ............... 604/367; 156/283, 62.8, 62.2; 442/411, 361, 337
See application file for complete search history.

(56) References Cited

U.S. PATENT DOCUMENTS

| | | | |
|---|---|---|---|
| 2,075,189 A | 3/1937 | Galligan et al. |
| 3,025,199 A | 3/1962 | Harwood |
| 3,848,594 A | 11/1974 | Buell |
| 3,860,003 A | 1/1975 | Buell |
| 3,911,173 A | 10/1975 | Sprague, Jr. |
| 3,914,488 A | 10/1975 | Gorrafa |
| 3,929,135 A | 12/1975 | Thompson |
| 4,107,364 A | 8/1978 | Sisson |
| 4,209,563 A | 6/1980 | Sisson |
| 4,324,246 A | 4/1982 | Mullane et al. |
| 4,342,314 A | 8/1982 | Radel et al. |
| 4,381,781 A | 5/1983 | Sciaraffa et al. |
| 4,463,045 A | 7/1984 | Ahr et al. |
| 4,515,595 A | 5/1985 | Kievit et al. |

(Continued)

FOREIGN PATENT DOCUMENTS

WO      WO 97/45259 A1      12/1997

*Primary Examiner*—Tatyana Zalukaeva
*Assistant Examiner*—Ginger Chapman
(74) *Attorney, Agent, or Firm*—Dara M. Kendall; Ken K. Patel

(57) ABSTRACT

The present invention relates to absorbent articles having a topsheet, a backsheet, and an absorbent core between the topsheet and the backsheet. The backsheet comprises a moisture vapor permeable, substantially liquid impermeable composite sheet material includes a powder-bonded nonwoven web adhered to a moisture vapor permeable thermoplastic film. The nonwoven web includes a first layer comprised primarily of fibers that are compatible with an adhesive used to bond the web, and a second layer comprised of a blend of fibers, some of which are compatible with, and some of which are incompatible with the bonding adhesive and the thermoplastic film. A method for making the composite sheet material and an item of apparel made from the sheet material are also provided.

10 Claims, 4 Drawing Sheets

U.S. PATENT DOCUMENTS

| | | |
|---|---|---|
| 4,573,986 A | 3/1986 | Minetola et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,725,481 A | 2/1988 | Ostapchenko |
| 4,739,012 A | 4/1988 | Hagman |
| 4,785,996 A | 11/1988 | Ziecker et al. |
| 4,795,454 A | 1/1989 | Dragoo |
| 4,834,735 A | 5/1989 | Alemany et al. |
| 4,834,741 A | 5/1989 | Sabee |
| 4,842,666 A | 6/1989 | Werenicz |
| 4,845,583 A | 7/1989 | Zimmerman et al. |
| 4,846,815 A | 7/1989 | Scripps |
| 4,857,067 A | 8/1989 | Wood et al. |
| 4,868,062 A | 9/1989 | Hoeschele et al. |
| 4,869,724 A | 9/1989 | Scripps |
| 4,888,231 A | 12/1989 | Angstadt |
| 4,894,060 A | 1/1990 | Nestegard |
| 4,909,803 A | 3/1990 | Aziz et al. |
| 4,938,753 A | 7/1990 | Van Gompel et al. |
| 4,946,527 A | 8/1990 | Battrell |
| 4,988,345 A | 1/1991 | Reising |
| 5,006,394 A | 4/1991 | Baird |
| 5,147,345 A | 9/1992 | Young et al. |
| 5,151,092 A | 9/1992 | Buell et al. |
| 5,234,423 A | 8/1993 | Alemany et al. |
| 5,326,612 A | 7/1994 | Goulait |
| 5,330,458 A | 7/1994 | Buell et al. |
| 5,385,500 A | 1/1995 | Schmidt |
| 5,445,874 A | 8/1995 | Shehata |
| 5,518,801 A | 5/1996 | Chappell et al. |
| 5,669,798 A * | 9/1997 | Koczab ............... 442/362 |
| 5,938,648 A | 8/1999 | LaVon et al. |
| 6,187,696 B1 * | 2/2001 | Lim et al. ............... 442/77 |
| 6,410,465 B1 * | 6/2002 | Lim et al. ............... 442/389 |
| 6,569,274 B1 * | 5/2003 | Makoui et al. ........... 156/204 |

* cited by examiner

ABSORBENT ARTICLES UTILIZING BREATHABLE COMPOSITE SHEET

This application claim the benefit of provisional application 60/137,198 filed Jun. 2, 1999.

FIELD OF THE INVENTION

The present invention relates to absorbent articles such as diapers, adult incontinence garments, and feminine hygiene products. The present invention further relates to such absorbent articles having outer coverings having a thin moisture vapor permeable film and a multiple layer fibrous substrate that combine to form a composite sheet that is durable, strong, and flexible, that acts as a barrier to liquids, bacteria, viruses and odors, yet is also highly permeable to moisture vapor.

JOINT RESEARCH AGREEMENT

The Procter & Gamble Company and E.I. DuPont Nemours and Company.

BACKGROUND OF THE INVENTION

Various woven and nonwoven sheet materials used in making medical drapes, medical gowns and absorbent articles, such as diapers and sanitary napkins, must be comfortable, soft, pliable and substantially liquid impermeable. The sheet materials used in medical apparel and absorbent articles function to contain the discharged materials and/or to isolate these materials from the body of the wearer or from the wearer's garments and bed clothing. As used herein, the term "absorbent article" refers to devices which absorb and contain body exudates, and, more specifically, refers to devices which are placed against or in proximity to the body of the wearer to absorb and contain the various exudates discharged from the body. Absorbent articles include disposable diapers, incontinence briefs, incontinence undergarments, incontinence pads, feminine hygiene garments, training pants, pull-on garments, and the like.

An ideal sheet material for use in medical apparel and absorbent articles will exhibit a high moisture vapor transmission rate that will reduce the build up of heat and humidity inside garments and articles made from the material. The ideal sheet material will also exhibit excellent barrier properties so as to prevent the passage or seepage of fluids, and will even prevent the passage of bacteria and viruses. The ideal material must also be strong enough so that it does not rip or delaminate under normal usage conditions regardless of whether the material is dry or wet. Where the sheet material is to be used in apparel, it is also important that the material be flexible, soft and drapable. Finally, where the sheet material is to be used in medical apparel, it is important that the sheet not generate fiber lint that might contaminate a medical environment.

PCT Publication No. WO 97/45259, which is hereby incorporated herein by reference, discloses a breathable composite sheet material comprised of a moisture vapor permeable thermoplastic film adhered to a fibrous substrate. The breathable thermoplastic film is primarily comprised of a polymer material selected from the group of block copolyether esters, block copolyether amides and polyurethanes. The fibrous substrate is a nonwoven sheet made primarily of a polymer fibers that are not compatible with the film, such as a polyolefin fibers. The film is adhered to the fibrous substrate by extruding a layer of the molten film-forming polymer directly onto the fibrous substrate and then mechanically engages the film and the fibers of the substrate, as for example by pressing the molten film into the fibrous substrate in a nip formed between two rolls.

U.S. Pat. No. 5,445,874 discloses a waterproof, bloodproof and virus-proof laminate material suitable for use in protective apparel. The laminate is comprised of a moisture vapor permeable film adhered to a woven or nonwoven fabric. The preferred film is a thermoplastic polyester elastomer. The disclosed fabrics include nonwoven fabrics of polyester, nylon and polypropylene. U.S. Pat. No. 5,445,874 discloses that the film can be laminated to the fabric by powder adhesive lamination, hot melt lamination, or wet adhesive lamination.

Adhesive lamination, thermal lamination and extrusion coating methods have all been used to produce composite sheets of a fibrous nonwoven substrate and a moisture vapor permeable, substantially liquid impermeable film. It has been possible to make such composite sheets with good barrier properties so long as the moisture vapor permeable film is relatively thick (i.e., >25 microns). However, it has been difficult to make such composite sheets with thinner films without sacrificing important barrier properties. Very thin moisture vapor permeable films are desirable in a composite sheet because thinner films facilitate greater flux of moisture vapor through the composite sheet and because thinner films use less of the film material and are accordingly less expensive to produce.

Adhesive lamination is carried out in a post film formation step. For adhesive lamination to be feasible, the moisture vapor permeable film must have enough tensile strength and tear strength so that the film can be formed, wound onto a roll, and later unwound and handled during the adhesive lamination process. It is difficult to handle moisture vapor permeable films less than 25 microns (1 mil) in thickness during the adhesive lamination process without tearing the film or introducing defects into the film.

Thermal lamination of moisture vapor permeable films less than 25 microns thick has similarly resulted in composite sheet materials with inadequate barrier properties. When composite sheets are made by thermally laminating a thin film to a fibrous substrate, the thin film handling problems associated with adhesive lamination as described above are encountered. In addition, to carry out a thermal lamination, the film must be subjected to elevated temperatures and pressures so as to soften the film and force it into mechanical engagement with the fibrous substrate. Generally, the peel strength between the film and the fibrous substrate increases with increasing lamination temperatures and increasing nip pressures. Unfortunately, when moisture vapor permeable films with a thickness of less than 25 microns are subjected to the increased temperatures and pressures needed to obtain adequate peel strength in the composite sheet, small holes develop in the film such that the composite sheet does not exhibit the fluid barrier properties desired in a composite sheet for use in absorbent articles or medical apparel. These defects can result from the non-uniform temperature throughout the web during bonding or from high nip pressures.

A composite sheet with excellent tensile and peel strength, that does not emit loose fibers, can be produced using a carded web of staple fiber that is powder bonded with an adhesive that is compatible with the fibers of the web. The composite sheet is produced by extrusion coating the powder-bonded web with a molten thin film that is also compatible with the fibers of the web and the powder adhesive. "Compatibility" of thermoplastic materials is an art-recognized term that refers, generally, to the degree to which the thermoplastic materials are miscible and/or interact with each other. Similarly, "incompatible" materials, as used herein, means polymer materials that are substantially immiscible or do not interact with each other. Incompatible materials do not wet or adhere well to each other, even when heated.

A composite sheet, made from a powder-bonded web that has been extrusion coated with a film of a thermoplastic polymer compatible with the fibers of the web and the solidified powder adhesive, exhibits good tensile strength and low linting because the solidified powder adhesive binds all of the fibers in the web into a strong matrix. These sheets exhibit excellent peel strength because the film readily adheres to the compatible adhesive and fibers of the web. For example, excellent tensile strength, peel strength and linting resistance can be obtained where the film, the nonwoven and the adhesive are all comprised of polyester polymers. Unfortunately, the film layer in composite sheets of this type is so thoroughly and completely bonded to the nonwoven that the sheet has a stiff paper-like feel that is unsuitable for apparel or many kinds of absorbent articles.

Accordingly, there is a need for a composite sheet material that acts as a barrier to fluids, bacteria and viruses, yet is also highly permeable to moisture vapor. Such a moisture vapor permeable, fluid impermeable composite sheet material should be durable, strong, and low linting, while at the same time being soft, flexible and comfortable enough for use in apparel products and absorbent articles. There is a further need for such a composite sheet that can be produced in an economical fashion, i.e., film extrusion and lamination in one process. There is a corresponding need for absorbent articles utilizing such materials to provide such characteristics.

SUMMARY OF THE INVENTION

The present invention provides an absorbent article having a topsheet, a backsheet, and an absorbent core between the topsheet and the backsheet. The backsheet comprises a moisture vapor permeable, substantially liquid impermeable composite sheet material. The sheet material comprises a first fibrous nonwoven web having a first side and an opposite second side, and a second fibrous nonwoven web having a first side and an opposite second side. The first side of the second fibrous nonwoven web abuts the second side of the first fibrous nonwoven web, and the first and second fibrous nonwoven webs each are powder-bonded webs wherein the fibers of the first and second fibrous webs are bonded to the other fibers of such web by a synthetic adhesive permeating the first and second nonwoven fibrous webs. The first and second fibrous nonwoven webs are bonded to each other by the adhesive. A moisture vapor permeable thermoplastic film is bonded to the second side of the second fibrous nonwoven web. At least 90 weight percent of the fibers in the first fibrous nonwoven web are compatible with the adhesive, between 25 and 75 weight percent of the fibers in the second fibrous nonwoven web are compatible with the adhesive and the thermoplastic film, and between 75 and 25 weight percent of the fibers in the second fibrous nonwoven web are incompatible with the adhesive and the thermoplastic film. At least 50 weight percent of the polymer in the thermoplastic film is also compatible with the adhesive.

Preferably, the weight of the fibers in the second nonwoven fibrous web is between ¼ and 4 times the weight of the fibers in the first nonwoven fibrous web. It is also preferred that the film of the composite sheet have an average thickness of less than 25 microns, and more preferably less than 20 microns. The composite sheet ideally exhibits a peel strength of at least 0.1 N/cm, a hydrostatic head of at least 60 cm, and a moisture vapor transmission rate, according to the LYSSY method, of at least 1000 g/m$^2$/24 hr.

According to a preferred embodiment of the invention, the adhesive in the nonwoven web is a polyester polymer or polyester copolymer adhesive, and the moisture vapor permeable film is comprised of at least about 75% by weight of polymer selected from the group of block copolyether esters, block copolyether amides, copolyether imide esters, polyurethanes, polyvinyl alcohol, and combinations thereof. In the preferred embodiment, at least 90 weight percent of the fibers in the first fibrous nonwoven web are made of polymer selected from the group of polyester polymers and copolymers, between 25 and 75 weight percent of the fibers in the second fibrous nonwoven web are made of polymer selected from the group of polyester polymers and copolymers, and between 75 and 25 weight percent of the fibers in the second fibrous nonwoven web are made of polymer selected from the group of polyamides, polyolefins, acrylics, and cotton. The polyester polymers and polyester copolymers in the fibers of the preferred embodiment are preferably selected from the group of poly(ethylene terephthalate), poly(1,3-propylene terephthalate) and copolymers thereof. At least 10% of such polyester fibers may be shaped fibers having a scalloped-oval cross-section. According to a preferred embodiment of the invention, the moisture vapor permeable film is comprised of at least about 75% by weight of block copolyether esters, and more preferably the film consists essentially of a copolyether ester elastomer.

The composite sheet of the invention is substantially free of pinholes, and substantially no liquid passes through the sheet when tested according to the liquid seepage test. It is further preferred that the composite sheet prevent the passage of microbes when tested according to the ISO 11607 standard for sterile packaging materials and that the composite sheet prevents the passage of microbes and viruses with a diameter greater than 0.025 microns when tested according to ASTM F1671.

The moisture vapor permeable film of the composite sheet of the invention may have first and second layers, each of which are comprised of a different moisture vapor permeable thermoplastic polymer composition. The fist layer of such a moisture vapor permeable film may comprise at least 60% of the total weight of the film and may comprise a substantially hydrophilic layer, while the second layer of the moisture vapor permeable film may comprise a substantially hydrophobic layer, wherein the first layer of the moisture vapor permeable film is bonded to the second side of the second fibrous nonwoven web.

The present invention is also directed to an item of apparel or a protective cover comprising the composite sheet material described above.

The present invention also includes a method for making a moisture vapor permeable, substantially liquid impermeable composite sheet comprising a fibrous nonwoven bonded with a powder adhesive and a moisture vapor permeable thermoplastic film. The method includes the steps of: (a) providing a first fibrous nonwoven web having a first side and an opposite second side, at least 90 weight percent of the fibers in the first fibrous nonwoven web being compatible with the adhesive; (b) providing a second fibrous nonwoven web having a first side and an opposite second side, and abutting the first side of the second fibrous nonwoven web with the second side of the first fibrous nonwoven web, between 25 and 75 weight percent of the fibers in the second fibrous nonwoven web being compatible with the adhesive and the thermoplastic film, and between 75 and 25 weight percent of the fibers in the second fibrous nonwoven web being incompatible with the adhesive and the thermoplastic film; (c) permeating a powder adhesive throughout the first and second fibrous nonwoven webs; (d) heating the web to a temperature sufficient to powder-bond the webs in a manner such that the fibers of the first and second fibrous webs are bonded to the other fibers of such web by the adhesive permeating the first and second nonwoven fibrous webs, and the first and second fibrous nonwoven webs are bonded to each other by the adhesive; (e) melt extruding a moisture vapor permeable thermoplastic film onto the second side of the second fibrous nonwoven web; (f) subjecting the composite sheet material to a confining pressure by passing the composite sheet material through a nip; and (g) collecting the sheet material onto a roll.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

Reference will now be made in detail to the presently preferred embodiments of the invention, examples of which are illustrated below.

Breathable Composite Sheet Materials

The composite sheet of the invention is comprised of a moisture vapor permeable film adhered to a fibrous substrate. Such composite sheets are sometimes referred to as laminate structures. Preferably, the fibers of the fibrous substrate are carded staple fibers held together by an adhesive that is applied to the web as a powder and subsequently heated so as to bind the fibers into a fiber matrix. The preferred film is a moisture vapor permeable thermoplastic film that can be extrusion coated as a melt directly onto the fibrous web in a manner such that a thin film adheres to the fibers of the web and to the adhesive that has been incorporated into the web.

It has been found that a composite sheet comprised of a film thermally laminated to a fibrous matrix can be made softer and more flexible if a substantial portion of the fibers in the fibrous substrate are made of a polymer that is not readily compatible with the polymer in the film and the adhesive. Unfortunately, laminate structures in which a substantial portion of fibers of the web are incompatible with the adhesive used to bind the fibers of the web have substantially reduced tensile strength and they tend to give off loose fibers.

The present invention is directed to a soft and flexible composite sheet with excellent tensile strength and resistance to fiber linting. According to the invention, the fibrous web of the composite sheet has at least two layers. A first layer is comprised of fibers in which at least 90 weight percent of the fibers are compatible with the adhesive used to bind the fibers of the web. A second layer of fibers deposited on the first layer of fibers is comprised of a blend of fibers in which between 25 to 75 weight percent of the fibers are incompatible with the adhesive used to bind the fibers of the web and between 75 and 25 weight percent of the fibers are compatible with the adhesive. The composite sheet further includes a thin moisture vapor permeable film that is extrusion coated directly onto the exposed surface of the second layer, which film is comprised of a thermoplastic polymer that is compatible with the adhesive used to bind the fibers of the web.

Figure 1:
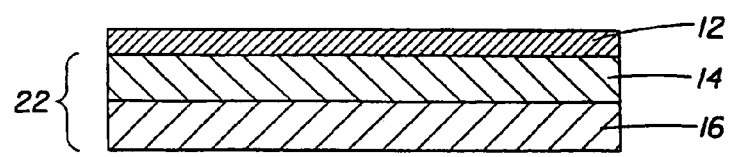
FIG. 1 is a cross-sectional view of the composite sheet structure of the invention.

Referring to FIG. 1, the composite sheet 10 of the current invention is shown. Sheet 10 comprises a moisture vapor permeable multi-layer nonwoven web 22 comprising fibrous nonwoven layers. A first nonwoven layer 16 abuts a second nonwoven layer 14. A powder adhesive introduced into the multi-layer web bonds the fibers within each layer to each other and bonds the fibrous layers 14 and 16 to each other. The fibers in the first nonwoven layer preferably comprise between 20 and 80 percent, by weight, of the fibers in the multi-layer web. The fibers in the second nonwoven layer also preferably comprise between 80 and 20 percent, by weight, of the fibers in the multi-layer web. More preferably, the fibers of the first nonwoven layer comprise between 40% and 75% by weight of the fibers in the multi-layer web, and the fibers of the second nonwoven layer comprise between 60% and 25% by weight of the fibers in the multi-layer web. A liquid impermeable, moisture vapor permeable polymer film 12 is extrusion coated onto the second nonwoven layer 14. Film 12 can be a single layer or multi-layer film.

The second nonwoven layer 14 is preferably a carded web comprising a blend of first and second staple fiber components. The first staple fiber component is comprised of fibers made of a first polymer that is compatible with the polymers of both the moisture vapor permeable film layer and the powder adhesive. The second staple fiber component is comprised of fibers made of a second polymer that is incompatible with the polymer of film layer 12 and the powder adhesive. The compatible staple fiber component of the second nonwoven layer 14 preferably comprises between about 25 and 75 weight percent of the fibers of the second nonwoven layer, and more preferably between about 40 and 60 weight percent of the fibers of the second nonwoven layer. According to alternative embodiments of the invention, the first compatible staple fiber component may comprise a mixture of two or more types of fibers that are each made of a polymer that is compatible with the adhesive, it may comprise fibers made from blends of polymers that are compatible with the adhesive, or it may comprise some mixture of the two. Likewise, the incompatible second staple fiber component of the second nonwoven layer 14 may comprise a mixture of two or more types of fibers that are each made of a polymer that is incompatible with the adhesive, it may comprise fibers made from blends of polymers that are incompatible with the adhesive, or it may comprise some mixture of the two. The second nonwoven film layer 14 may alternatively be comprised of two or more sub-layers, each of which are comprised of between 25 and 75 weight percent of the compatible staple fiber component and between 75 and 25 weight percent of the incompatible staple fiber component.

At least 90 weight percent of the staple fibers in the first nonwoven layer 16, and more preferably between 95 and 100 weight percent of the staple fibers in the first nonwoven layer 16, are made of a polymer that is compatible with both the powder adhesive and the first staple fiber component of the second nonwoven layer. The staple fibers of the first nonwoven layer 16 may be identical to the compatible first staple fiber component of the second nonwoven layer 14. The first nonwoven fiber layer 16 may alternatively be comprised of two or more sub-layers, each of which are comprised of at least 90 weight percent of fibers made of polymers that are compatible with the powder adhesive and the first staple fiber component of the second nonwoven layer.

The powder adhesive that is used to powder-bond the nonwoven layers is comprised of a thermoplastic polymer that melts at a temperature below the melting point of the staple fibers used in the fibrous nonwoven layers. The powder adhesive is compatible with the film layer, the first staple fiber component of the second nonwoven layer 14, and the staple fibers of the first nonwoven layer 16 so as to provide good adhesive bonding with the compatible fibers and the film layer when applied. The powder adhesive is distributed throughout both the first and second nonwoven layers to provide bonding both within and between the nonwoven layers.

The fiber blend in the second nonwoven layer 14 gives rise to discrete bonding between the fibrous web and the film layer 12. This discrete bonding results because the incompatible fibers do not bond well with the film layer whereas the compatible fibers do. This discrete bonding improves the drapeability of the fabric, provides a more fabric-like texture versus film-like or paper-like texture, and results in a fabric that is softer, more flexible, and less noisy than composite sheets where the nonwoven substrate is comprised primarily of fibers that are compatible with the film layer. These properties are particularly desirable for apparel and absorbent article end uses. Because the powder adhesive does not bond well to the incompatible fiber component of the second nonwoven layer 14, the strength of the second nonwoven layer alone would tend to be lower than is desired for many end uses. However, because the powder adhesive is compatible with at least 90 weight percent of the fibers of the first nonwoven layer 16, good adhesive bonding is achieved throughout the first nonwoven layer of the web. This results in a composite sheet that exhibits good overall strength and durability (e.g. abrasion resistance). In addition, good adhesive bonding is obtained between the first and second nonwoven layers.

Film layer 12 of the composite sheet structure 10 is a moisture vapor permeable and substantially liquid impermeable film. The film layer is preferably extruded and laminated onto the fibrous substrate 22 in a single process. Film layer 12 comprises a thermoplastic polymer material that can be extruded as a thin, continuous, nonporous, substantially liquid impermeable, moisture vapor permeable film. Preferably, the extruded film is less than 25 microns thick, and more preferably less than 15 microns thick, and most preferably less than 10 microns thick. The film layer 12 is preferably comprised of a block polyether copolymer such as a block polyether ester copolymer, a polyetheramide copolymer, a polyurethane copolymer, a poly(etherimide) ester copolymer, polyvinyl alcohols, or a combination thereof. Preferred copolyether ester block copolymers are segmented elastomers having soft polyether segments and hard polyester segments, as disclosed in Hagman, U.S. Pat. No. 4,739,012. Suitable copolyether ester block copolymers are sold by DuPont under the name Hytrel®. Hytrel® is a registered trademark of DuPont. Suitable copolyether amide polymers are copolyamides available under the name Pebax® from Atochem Inc. of Glen Rock, N.J., USA. Pebax® is a registered trademark of Elf Atochem, S.A. of Paris, France. Suitable polyurethanes are thermoplastic urethanes available under the name Estane® from The B.F. Goodrich Company of Cleveland, Ohio, USA. Suitable copoly(etherimide) esters are described in Hoeschele et al. U.S. Pat. No. 4,868,062.

Alternatively, the film layer 12 may be comprised of a blend of polymers in which at least 50% by weight of the film is comprised of polymers that are incompatible with the adhesive used to bind the fiber of the web 22. More preferably, the film layer 12 is comprised of at least 75% by weight of polymers selected from the group of block copolyether esters, block copolyether amides, copolyether imide esters, polyurethanes, and polyvinyl alcohol.

The compatible fibrous components of the second nonwoven layer 14 and the fibers of the first nonwoven layer 16 preferably comprise a polyester such as poly(ethylene terephthalate), poly(1,3-propylene terephthalate) and copolymers thereof. Such polyester polymers are compatible with block polyether copolymers such as a block polyether ester copolymers, with polyetheramide copolymers, with polyurethane copolymers, with poly(etherimide) ester copolymers, and with combinations thereof. The incompatible fibrous components of the second nonwoven layer 14 are preferably polyamides such as poly(hexamethylene adipamide) (nylon 66) and polycaproamide (nylon 6), polyolefins such as polypropylene or polyethylene, acrylic polymers, or cotton. Preferred nonwoven materials for the second nonwoven layer 14 of the fibrous web 22 include blends of polyolefin and polyester fibers and blends of polyamide and polyester fibers. One type of polyester fiber that can be used in the first and/or second nonwoven layers of the fibrous web 22 are shaped polyester fibers with a scalloped-oval cross-section as disclosed in U.S. Pat. No. 3,914,488 to Garrafa (assigned to DuPont), which is hereby incorporated by reference. It is believed that where the polyester fibers comprise at least 10% of such shaped fibers, channels are created in the fibrous substrate through which moisture vapor can be more efficiently conveyed through the composite sheet.

Where the composite sheet material is intended for use in apparel, the staple fiber components of the first and second nonwoven layers are preferably selected so as to have some degree of hydrophobicity. Fibers having hydrophilic finishes applied thereto are generally less preferred. Hydrophilic fibers can contribute to soaking of the nonwoven layer by fluids, such as blood, by capillary action when the fluid contacts the edge of the fabric, such as may occur with the sleeve of a medical garment. Very fine fibers (low dtex per filament) have also been found to contribute to this problem. Preferably the staple fibers are larger than about 1 denier per filament (1.1 dtex), and more preferably larger than 1.5 denier per filament (1.65 dtex), where the composite sheet material is to be used in apparel.

The nonwoven fibrous web 22 should exhibit strength, permeability, and softness properties that are desired for the end use for which the composite sheet is to be applied. For example, where the composite sheet 10 is to be used in an absorbent article, the fibrous composite web 22 should preferably have a tensile strength of at least 1 N/cm and an elongation of at least 30% in both the machine and cross directions. The machine direction is the long direction within the plane of the sheet, i.e., the direction in which the sheet is produced. The cross direction is the direction within the plane of the sheet that is perpendicular to the machine direction. More preferably, the fibrous webs should have a tensile strength of at least 1.5 N/cm and an elongation of at least 50% in both the machine and cross directions. Preferably, the fibrous web is a porous structure that enhances both moisture permeability through the composite sheet and physical bonding between the film and web layers of the composite sheet.

Powder adhesives suitable for preparing the powder bonded-nonwoven layer are preferably polyester copolymer powders such as those available from EMS-American Grilon, Inc. The bonding powder should have a lower melting point than the fibers in the web. In general, the bonding powder will be a thermoplastic material and it should be capable of forming a good adhesive bond with the fibers being used. In the case of polyester fibers, it is particularly preferred to use a polyester or copolyester bonding powder. Typical copolyester adhesives have melting points of from 100 to 130° C. and are available as coarse powders (200–420 microns or 70-40 U.S. standard mesh), medium powders (80–200 microns or 200-70 U.S. standard mesh) and fine powders (80 microns or less, or finer than 200 U.S. standard mesh), the medium powders being preferred when using mechanical applicators.

The powder-bonded nonwoven web 22 used in the composite sheet of the invention is prepared using methods known in the art, such as that described in Zimmerman et al. U.S. Pat. No. 4,845,583. The second nonwoven layer 14, comprising a blend of compatible and incompatible fibers, is laid on top of the first nonwoven layer 16 and the combined layers are optionally passed through a web spreading section prior to applying the powdered adhesive material. The adhesive powder is applied to the nonwoven web using a powder-depositing device. The powder drops onto the web and is distributed through the web by gravity. Excess powder falls through the web and is collected for recycling. The amount of powder deposited in the nonwoven web is preferably from about 8 to about 30 percent of the total combined weight of the nonwoven layers of the web, and preferably between about 15 to 25 weight percent. Bonding of the nonwoven layers can be achieved by passing the web through an oven, such as an infrared oven in which the adhesive powder fuses and bonds the fibers of the web at fiber crossover points where the fibers and the bonding material come into contact. Upon leaving the oven, the web is subjected to light pressure by means of a nip roll.

The mixing of the thermoplastic polymer or blends of polymers that comprise the film layer 12 of the composite sheet of the invention can be conducted according to methods and techniques known in the art, e.g., by physical tumble blending followed by extrusion and mixing in a single screw extruder equipped with a mixing head such as those available from Davis-Standard Corp. (Pawcatuck, R.I., USA) or a twin screw compounding extruder such as those available from Warner-Pfliederer (Ramsey, N.J., USA) and Bersdorf Corporation (Charlotte, N.C., USA). Alternatively, loss in weight or volumetric feeders such as those available from K-Tron America (Pitman, N.J., USA) may be used to control the composition being fed to the extruders.

The film layer 12 is preferably applied to the second nonwoven layer of the powder-bonded fibrous web by extrusion-coating. In the extrusion coating process, a uniform molten extrudate is coated on the powder-bonded fibrous web. The molten polymer and the web are brought into more intimate contact as the molten polymer cools and bonds with the web. Such contact and bonding can be enhanced by passing the layers through a nip formed between two rolls. Alternatively, the molten polymer can be pulled into contact with the fibrous web by passing the coated web over a suction inlet such that a vacuum pulls the molten polymer into contact with the web as the polymer cools and bonds with the web. During the extrusion coating process, some or all of the powder adhesive is re-melted and provides improved bonding between the thin film layer and the fibrous web. The bonding between the adhesive present in the web and the polymer in the film makes it easier to produce a very thin moisture vapor permeable film that is substantially free of pinholes or other defects, yet still has a relatively high rate of moisture vapor transmission. As used herein, "pinholes" means small holes inadvertently formed in a film either during manufacture or processing of the film.

Figure 2:
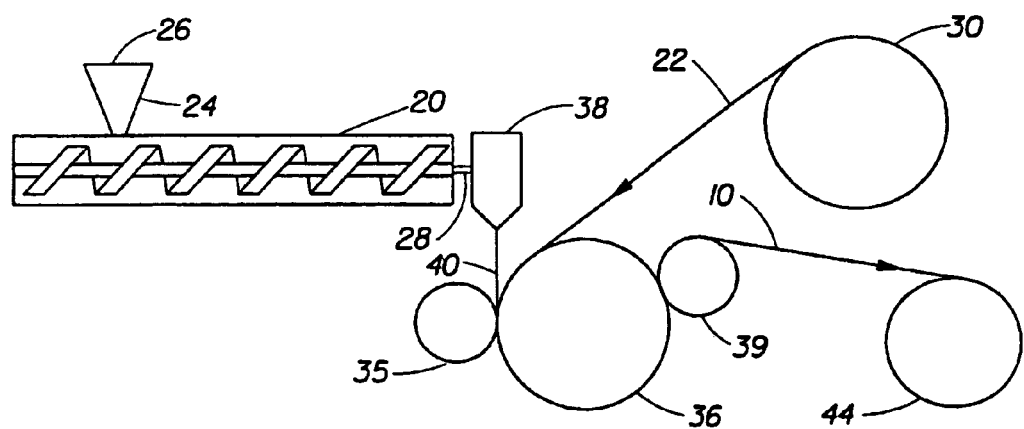
FIG. 2 is a schematic representation of a process by which the composite sheet structure of the invention can be made.

One preferred means for applying the film layer to the powder bonded nonwoven web is illustrated in FIG. 2. Thermoplastic polymer is fed in pellet form, along with any additives, into an inlet 26 of an extruder hopper 24, preferably under a nitrogen purge. The polymer is melted and mixed in a screw extruder 20 at a screw speed in the range of 100 to 200 rpm, depending on the dimensions of the extruder and the properties of the polymer. The melted mixture is discharged from the extruder under pressure through a heated line 28 to a flat film die 38. The polymer is discharged from the flat film die 38 at a temperature above the melting temperature of the polymer, and preferably at a temperature in the range of 180° C. to 240° C. The polymer melt 40 discharging from the flat film die 38 coats the powder bonded fibrous nonwoven web 22 provided from supply roll 30.

Preferably, the fibrous web 22 passes under the die at a speed that is coordinated with the speed of the extruder so as to obtain a very thin film that preferably has a thickness of less than 25 microns. The coated web enters a nip formed between nip roll 35 and roll 36, which rolls are maintained at a temperature selected to obtain a composite sheet with a desired peel strength and moisture vapor permeability. The temperature of rolls 35 and 36 is preferably within the range of 10° C. to 120° C. Higher roll temperatures yield a composite sheet having a higher peel strength, while lower roll temperatures yield composite sheets with a higher moisture vapor permeability. Preferably, nip roll 35 is a smooth rubber roll with a low-stick surface coating while roll 36 is a metal roll. Nip roll 35 can also have a matte or textured finish to prevent sticking of the film layer. A textured embossing roll may be used in place of the metal roll for the roll 36 if a composite sheet with a more textured film layer is desired. Passing the coated web through the nip formed between cooled rolls 35 and 36 quenches the polymer melt while at the same time pressing the polymer melt 40 into contact with the fibers and adhesive of the fibrous web 22. The nip pressure applied should be sufficient to get the desired bonding between the film and the nonwoven but not so great as to create pinholes in the film layer. The coated composite 10 is transfered from the roll 36 to another smaller roll 39 before being wound up on a collection roll 44.

The second nonwoven layer 14 of the fibrous web 22 is preferably made with a smooth exposed surface from which substantially few fibers extend out from the plane of the fibrous web. This smooth surface of the web is important when laminating a very thin film (<25 microns) to the fibrous web. If the film is laminated to the surface of a fibrous web that is not relatively smooth, fibers that protrude out from the plane of the web will likely protrude through the film, which may create pinholes and thereby allow liquid seepage through the composite sheet.

The film layer 12 of the composite sheet can be comprised of multiple layers. Such a film may be co-extruded with layers comprised of one or more of the above described thermoplastic film materials. Examples of such multiple layer moisture vapor permeable films, which typically comprise a comparatively more hydrophobic elastomer layer and a comparatively more hydrophilic elastomer layer, are disclosed in Ostapchenko, U.S. Pat. No. 4,725,481, which is hereby incorporated by reference. In a preferred embodiment, the multiple layer film (in a bi-layer execution) is extruded onto the second nonwoven layer 14 of the composite fibrous web 22 with the comparatively more hydrophobic elastomer layer facing outwardly from the web and the comparatively more hydrophilic elastomer layer bonded to the second nonwoven layer of the fibrous web. Typically, for a given thickness, the hydrophobic elastomer layer exhibits a lower moisture vapor transmission rate than the hydrophilic elastomer layer due to its comparatively lower moisture content under in-use conditions. However, when employed in a comparatively thin layer, the effect of the hydrophobic lower moisture content film layer does not significantly diminish the moisture vapor transmission rate of the overall composite sheet. Preferably, the comparatively more hydrophobic elastomer comprises between 20 and 30 percent of the total thickness of the composite film layer. In medical garment end uses, the garment can be manufactured with the film layer facing outwardly, away from the person wearing the garment. The outer, comparatively more hydrophobic layer swells less when contacted with aqueous materials resulting in less puckering of the fabric when contacted with aqueous materials. Because the majority of the film layer is comprised of the comparatively more hydrophilic layer, the garment also maintains an excellent moisture vapor transmission rate to ensure the comfort of the wearer.

Figure 3:
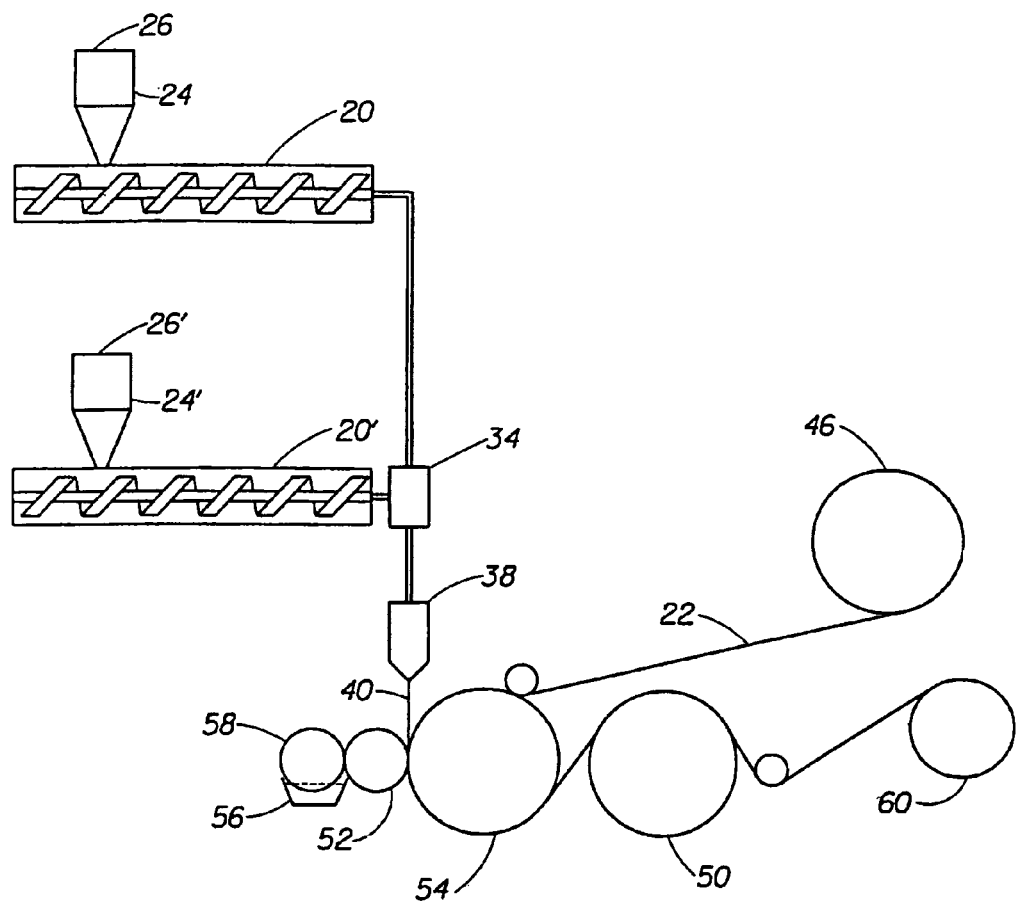
FIG. 3 is a schematic representation of another process by which the composite sheet structure of the invention can be made.

FIG. 3 illustrates a process for extrusion coating of a two-layer film on a powder-bonded nonwoven web. A first thermoplastic polymer is fed in pellet form, along with any additives, into the inlet 26 of extruder hopper 24, while a second thermoplastic polymer is fed in pellet form, along with any additives, into the inlet 26' of extruder hopper 24'. The polymer is melted and mixed in the screw extruders 20 and 20' at screw speeds that depend on the dimensions of the extruders and the properties of the polymer. The melted mixture is discharged from the extruder under pressure through heated lines to a melt combining block 34, where a multiple layer melt is formed that is extruded as a multiple layer film through flat film die 38. The polymer is discharged from the flat film die 38 at a temperature above the melting point of the polymer mixture, and preferably at a temperature in the range of 180° C. to 240° C. The polymer melt 40 discharging from the flat film die 38 coats the powder-bonded fibrous web 22 provided from a supply roll 46.

Preferably, the powder-bonded fibrous web 22 passes under the die 38 at a speed that is coordinated with the speed of the extruder so as to obtain a very thin film thickness of less than 25 microns. The coated web enters a nip formed between nip roll 52 and roll 54, which rolls are maintained at a temperature selected to obtain a composite sheet with a desired peel strength and moisture vapor permeability. A water dip pan 56 with associated roll 58 can be used to increase the quench rate and to prevent sticking. Alternatively, a water mist applied to the film layer or a water bath associated with roll 52 may be used. An optional cooled quench roll 50 can be used to provide additional cooling prior to winding the composite sheet product on collection roll 60.

When used for garment end uses such as medical gowns, the extrusion-coated powder-bonded nonwoven composite preferably has a basis weight of about 1.2 to 3 oz/yd$^2$ (41 to 102 g/m$^2$) and a grab tensile strength of at least 11 lb/inch (1925 N/m), and more preferably at least 15 lb/inch (2625 N/m) in both the machine and cross directions. When used for diapers, the powder-bonded multi-layer nonwoven composite preferably has a basis weight of about 0.5 to 0.7 oz/yd$^2$ (17 to 24 g/m$^2$) and a tensile strength of at least 2.2 lb/inch (386 N/m) in the machine direction and at least 0.8 lb/inch (140 N/m) in the cross direction. The powder-bonded composite sheet material of the current invention has a significantly higher hydrostatic head than similar fabrics prepared using a thermally bonded nonwoven layer. The moisture vapor transmission rate of the fibrous web may be reduced slightly when a powder-bonded nonwoven is used. However, the use of a powder-bonded web results in improved bonding between the nonwoven web and the film layer compared to fabrics where the nonwoven layer comprises a thermally-bonded nonwoven, such that thinner film layers without pinholes are possible. Use of thinner film layers results in an increase in the moisture vapor transmission rate and a small reduction in hydrostatic head, with the final powder-bonded composite having a higher moisture vapor transmission rate and hydrostatic head than thermally-bonded nonwovens coated with films of greater thickness (See Example 1 and Comparative Example A below).

In an alternative embodiment of the invention, the composite sheet structure may be comprised of a moisture vapor permeable film layer with two fibrous webs like the composite web 22 described above, adhered on opposite sides of the film layer. In this alternative embodiment of the invention, the second nonwoven layer of each of the fibrous webs, which layer is comprised of a blend of fibers that are compatible and incompatible with the film layer, would be bonded directly to opposite sides of the film layer in a manner similar to that described above.

TEST METHODS

In the description above and in the non-limiting examples that follow, the following test methods were employed to determine various reported characteristics and properties. ASTM refers to the American Society for Testing and Materials, TAPPI refers to the Technical Association of Pulp and Paper Industry, and ISO refers to the International Organization for Standardization. Additional suitable test methods, including those suitable for evaluating the product performance characteristics of absorbent articles, are disclosed in commonly-assigned, co-pending (allowed) U.S. patent application Ser. No. 08/984,463, filed Dec. 3, 1997 in the names of LaVon et al., and entitled "Absorbent Articles Exhibiting Improved Internal Environmental Conditions", the disclosure of which is hereby incorporated herein by reference.

Basis weight was determined by ASTM D-3776, which is hereby incorporated by reference, and is reported in g/m$^2$.

Tensile strength was determined by ASTM D 5035-95, which is hereby incorporated by reference, with the following modifications. In the test a 2.54 cm by 20.32 cm (1 inch by 8 inch) sample was clamped at opposite ends of the sample. The clamps were attached 12.7 cm (5 in) from each other on the sample. The sample was pulled steadily at a speed of 5.08 cm/min (2 in/min) until the sample broke. The force at break was recorded in pounds/inch and converted to Newtons/cm as the breaking tensile strength.

Film thickness was determined by ASTM Method D177-64, which is hereby incorporated by reference, and is reported in microns.

Grab Tensile Strength was determined by ASTM D 5034-95, which is hereby incorporated by reference, was measured in pounds/inch and is reported in Newtons/cm.

Elongation to Break of a sheet is a measure of the amount a sheet stretches prior to failure (breaking)in a strip tensile test. A 1.0 inch (2.54 cm) wide sample is mounted in the clamps—set 5.0 inches (12.7 cm) apart—of a constant rate of extension tensile testing machine such as an Instron table model tester. A continuously increasing load is applied to the sample at a crosshead speed of 2.0 in/min (5.08 cm/min) until failure. The measurement is given in percentage of stretch prior to failure. The test generally follows ASTM D 5035-95.

Peel strength is measured according to a test that generally follows the method of ASTM D2724-87, which is hereby incorporated by reference. The test was performed used a constant rate of extension tensile testing machine such as an Instron table model tester. A 2.54 cm (1.0 in) by 20.32 cm (8.0 in) sample is delaminated approximately 3.18 cm (1.25 in) by initiating a separation between the fibrous web and the moisture vapor permeable film. The separated sample faces are mounted in the clamps of the tester which are set 5.08 cm (2.0 in) apart. The tester is started and run at a cross-head speed of 50.8 cm/min (20.0 in/min). The computer starts picking up readings after the slack is removed, nominally a 5 gram pre-load. The sample is delaminated for about 12.7 cm (5 in) during which sufficient readings are taken to provide a representative average of the data. The peak load and average peel strength is given in N/cm. For samples that are peeled the entire 5 inches the average peel strength is considered to be the peel strength. For samples that do not peel the entire 5 inches due to either full bond conditions or failures in the substrates, the peak load is considered to be the peel strength.

Hydrostatic head was measured according to AATCC Test Method 127, which measures the resistance to water penetration on a 7 in×7 in (18 cm×18 cm) test sample. Water pressure is applied to the fabric side of the test specimen until the sample is penetrated by water at three places. The hydrostatic pressure is measured in inches and converted to SI units and is reported in cm of water. The equipment used to measure hydrostatic head is made by Aspull Engineering Ltd, England.

Water Absorption is measured according to ASTM D570, which is hereby incorporated by reference.

Moisture Vapor Transmission Rate (MVTR) is reported in $g/m^2/24$ hrs and was measured using MVTR data acquired by ASTM E398-83 that was collected using a LYSSY MVTR tester model L80-4000J. LYSSY is based in Zurich, Switzerland. MVTR test results are highly dependent on the test method used and material type. Important variables between test methods include pressure gradient, volume of air space between liquid and sheet sample, temperature, air flow speed over the sample and test procedure. ASTM E398-83 (the "LYSSY" method) is based on a pressure gradient of 85% relative humidity ("wet space") vs. 15% relative humidity ("dry space"). The LYSSY method measures the moisture diffusion rate for just a few minutes and under a constant humidity delta, which measured value is then extrapolated over a 24 hour period.

Viral Barrier properties were measured according to ASTM F1671, which is hereby incorporated by reference. ASTM F1671 is a standard test method for measuring the resistance of materials used in protective clothing to penetration by blood-borne pathogens. According to this method, three samples of a sheet material being tested are challenged with $10^8$ Phi-X174 bacteriophage, similar in size to the Hepatitis C virus (0.028 microns) and with a surface tension adjusted to 0.042 N/m, at a pressure differential of 2 psi (13.8 kPa) for a 24 hour period. Penetration of the sample by viable viruses is determined using an assay procedure. The test results are reported in units of Plaque Forming Units per milliliter PFU/ml. A sample fails if any viral penetration is detected through any of the samples. A sample passes if zero PFU/ml were detected after the 24 hour test period.

A positive and negative control is run with each sample set. The positive control was a microporous membrane with a pore size of 0.04 microns which passed 600 PFU/ml. The negative control was a sheet of Mylar® film, which passed 0 PFU/ml.

Liquid Seepage is detected using a solution of 70 parts isopropyl alcohol, 30 parts water and 1 part red dye food color. According to this test, a sheet of a white absorbent blotting material measuring about 89 cm by 61 cm (35 in by 24 in) is placed on a flat surface and covered with a test sample of the same dimensions with the substrate side of the sample facing up. A 250 ml portion of the solution is poured on top of the test sample and covered with a template measuring about 46¾ cm by 46¾ cm (18 in by 18 in). A 4.5 kg (10 lb) weight is placed on top of the template for 10 minutes after which the weight, template and test sample are removed from the white blotting paper. The paper is then inspected for ink spots to determine whether seepage occurred.

Bacterial barrier is measured according to ISO 11607 which states under section 4.2.3.2 that a material that is impermeable to air for one hour (according to an air porosity test) satisfies the standard's microbial barrier requirements. With regard to porous materials, section 4.2.3.3 of ISO 11607 states that there is no universally applicable method of demonstrating microbial barrier properties in porous materials, but notes that the microbial barrier properties of porous materials is typically conducted by challenging samples with an aerosol of bacterial spores or particulates under a set of test conditions which specify the flowrate through the material, microbial challenge to the sample, and duration of the test. One such recognized test is ASTM F 1608-95.

EXAMPLES

The following non-limiting examples are intended to illustrate the product and process of the invention and not to limit the invention in any manner.

Film Components

The individual components in the film compositions described in the examples below were as follows:

Hytrel® G4778 is a copolyether ester thermoplastic elastomer sold by DuPont, and having a melting point of 208°

C., a vicat softening temperature of 175° C., a shore hardness of 47D, and a water absorption of 2.3%.

Hytrel® HTR 8206 is a copolyether ester thermoplastic elastomer sold by DuPont, and having a melting point of 200° C., a vicat softening temperature of 151° C., a shore hardness of 45D, and a water absorption of 30%.

Hytrel® HTR 8171 is a copolyether ester thermoplastic elastomer sold by DuPont, and having a melting point of 150° C., a vicat softening temperature of 76° C., a shore hardness of 32D, and a water absorption of 54%.

$TiO_2$ Concentrate was a concentrate of 50% by weight particulate titanium dioxide pigment in high density polyethylene. The $TiO_2$ is added to make the film layer opaque.

A Hytrel® 8206/8171 blend was prepared by dry blending the copolyether ester thermoplastic elastomers and the titanium dioxide concentrate.

Examples 1–2

A bi-layer fibrous nonwoven web was produced from two carded webs by powder bonding. The first layer was a carded web of a blend of 50 weight percent poly(ethylene terephthalate) (PET) staple fiber (Dacron® Type 54W polyester fiber, 1.5 inch (3.8 cm) cut length, 1.5 denier (1.65 dtex), manufactured by DuPont) and 50 weight percent polypropylene staple fibers (1.5 inch (3.8 cm)) cut length, 2.8 denier per filament (3.08 dtex), T-198 polypropylene fiber manufactured by FiberVision Company). The second layer was a carded web of 100% poly(ethylene terephthalate) staple fiber (Dacron® 90S PET, 1.5 inch cut length, 2.25 denier, manufactured by DuPont). The first layer was placed on top of the second layer, the combined layers passed through a web-spreading section for a final basis weight for each layer of 0.28 oz/yd² (9.5 g/m²), and a copolyester powder adhesive (Griltex® DS1371, obtained from EMS-American Grilon, Inc.) having a melting point of between 99° C. and 105° C. was applied to the combined nonwoven layers at 0.14 oz/yd² (4.7 g/m²). The web was then passed through an infrared oven and heated to melt the powder adhesive, and then through a nip which applied a light pressure. The basis weight of the final powder-bonded nonwoven substrate was 0.7 oz/yd² (23.7 g/m²).

The powder-bonded composite nonwoven layer was extrusion coated with a two-layer Hytrel® copolyether ester film as shown in FIG. 3. The first film layer, extruded adjacent the first (fiber blend) nonwoven layer of the web, was a blend of 46 wt % Hytrel® 8206, 48 wt % Hytrel® 8171, and 6 wt % of the $TiO_2$ concentrate, and comprised approximately 80% of the total thickness of the film layer, based on scanning electron micrographs. The second (top) film layer was Hytrel® G4778 and comprised approximately 20% of the total thickness of the film layer. The components of the first film layer were mixed and fed in pellet form into a 4 inch (10.2 cm) diameter screw extruder that was connected to the melt combining block. The Hytrel® G4778 for the second layer was fed in pellet form into a different 3 inch (7.6 cm) diameter screw extruder that was connected to the same melt combining block. The components for both film layers were each melted at a temperature of 440° F. (226° C.) and extruded to the melt combining block. The two layer melt was then fed to a 30 mil (762μ) by 102 cm die opening in a heated die block maintained at 232° C. A bi-layer film was extruded from the die opening and was coated on the powder-bonded composite nonwoven fibrous substrate. The powder-bonded nonwoven substrate was spaced about 12 inches (30.5 cm) below the opening of the die. The film was extruded at a constant rate in order to keep the 2-layer film thickness constant at 20 microns. The film was joined to the fibrous powder-bonded nonwoven substrate by passing the coated web through a pair of nip rolls. Nip roll 52, facing the polymer melt, was a silicone rubber roll having a matte finish. Quench roll 50 was maintained at 65° F. (18° C.).

The procedure of Example 1 was followed for Example 2 except that the line speed during film extrusion was adjusted to reduce the thickness of the 2-layer Hytrel® film from 20 microns to 15 microns.

The properties of the composite fabrics are reported below in Table 1. The results are discussed in Comparative Example A.

Comparative Example A

A bi-layer nonwoven fabric was produced by thermal-calender bonding of two carded staple nonwoven layers. The first nonwoven layer was a 0.35 oz/yd² (11.9 g/m²) carded web of a blend of 50 weight percent poly(ethylene terephthalate) staple fiber (Dacron® Type 54W polyester fiber, 1.5 inch (3.8 cm) cut length, 1.5 denier per filament (1.65 dtex), manufactured by DuPont) and 50 weight percent polypropylene staple fibers (1.5 inch cut length, 2.8 denier per filament (3.08 dtex), T-198 polypropylene fiber manufactured by FiberVision Company). The second nonwoven layer was a 0.35 oz/yd² (11.9 g/m²) carded web of 100% T-198 polypropylene staple fiber. The first carded web was placed on top of the second carded web and point-bonded with a thermal-calender bonder using a very light nip pressure to optimize drapeability.

The thermally-bonded composite nonwoven layer was extrusion coated with a bi-layer copolyether ester film using the process conditions and film layers described in Example 1. The properties of the composite fabric are reported below in Table 1.

The results shown in Table 1 demonstrate that for a film thickness of 20 microns, the fabric of the invention prepared using the powder-bonded nonwoven substrate has twice the peel strength in both the machine direction (MD) and cross direction (CD) compared to the fabric prepared using the thermally-bonded nonwoven substrate. In addition, the 20 micron thick fabric of the invention (Example 1) has greater than four times the hydrostatic head compared to Comparative Example A, with only a 7% reduction in MVTR. Example 2 demonstrates that by reducing the thickness of the Hytrel® polymer film layer by 25% to 15 microns, that a peel strength is achieved that is equivalent to Comparative Example A having a 20 micron thick film layer, while maintaining a hydrostatic head that is greater than 3 times that of Comparative Example A, and a MVTR that is 11% higher. A liquid moisture seepage test was performed by applying the food coloring/alcohol solution to the film side of the composite fabrics. Significantly fewer pinhole defects were detected with the powder-bonded nonwoven composite compared to the thermally-bonded nonwoven composite.

Example 3

A bi-layer fibrous nonwoven layer was produced from two carded webs by powder bonding. The first layer was a 0.40 oz/yd² (13.6 g/m²) carded web (basis weight measured after spreading during powder bonding process) of a blend of 50 weight percent poly(ethylene terephthalate) staple fiber (Dacron® Type 90S polyester fiber, 1.5 inch cut length (3.8 cm), 2.25 denier per filament (2.5 dtex), manufactured by DuPont) and 50 weight percent polyamide staple fibers (Type 200 nylon 6,6 staple manufactured by DuPont, 1.5 inch (3.8 cm) cut length, 1.8 denier (2.0 dtex)). The second layer was a 0.80 oz/yd$^2$ (27.1 g/m$^2$) carded web (basis weight measured after spreading during powder bonding process) of 100% poly(ethylene terephthalate) staple fiber (Dacron® 90S PET, 1.5 inch (3.8 cm) cut length, 2.25 denier per filament (2.5 dtex), manufactured by DuPont). The first layer was placed on top of the second layer and a copolyester powder adhesive (Griltex® DS1371, obtained from EMS-American Grilon, Inc.) having a melting point of between 99° C. and 105° C. was applied to the nonwoven at 0.3 oz/yd$^2$ (10.2 g/m$^2$). The nonwoven layers were powder bonded using the method described in Example 1. The basis weight of the final powder-bonded nonwoven substrate was 1.5 oz/yd$^2$ (50.9 g/m$^2$).

The powder-bonded composite nonwoven substrate was extrusion coated with a bi-layer copolyether ester film using the process conditions and film layers described in Example 1. The properties of the composite fabric are reported below in Table 1.

Example 4

A bi-layer fibrous nonwoven layer was produced from two carded webs by powder bonding. The first layer was a 0.28 oz/yd$^2$ (9.5 g/m$^2$) (basis weight measured after spreading during powder bonding process) carded web of a blend of 50 weight percent poly(ethylene terephthalate) staple fiber (Dacron® Type 54W polyester fiber, 1.5 inch (3.8 cm) cut length, 1.5 denier per filament (1.65 dtex), manufactured by DuPont) and 50 weight percent polyamide staple fibers (Type 200 nylon 6,6 staple manufactured by DuPont, 1.5 inch (3.8 cm) cut length, 1.8 denier (2.0 dtex)). The second layer was a 0.96 oz/yd$^2$ (32.6 g/m$^2$) (basis weight measured after spreading during powder bonding process) carded web of 100% poly(ethylene terephthalate) staple fiber (Dacron® 90S PET, 1.5 inch (3.8 cm) cut length, 2.25 denier per filament (2.5 dtex), manufactured by DuPont). The first layer was placed on top of the second layer and a copolyester powder adhesive (Griltex® DD1371, obtained from EMS-American Grilon, Inc.) having a melting point between 99° C. and 105° C. was applied to the nonwoven at 0.3 oz/yd$^2$ (10.2 g/m$^2$). The nonwoven layers were powder bonded using the method described in Example 1. The basis weight of the final powder-bonded nonwoven substrate was 1.54 oz/yd$^2$ (52.2 g/m$^2$).

The powder-bonded composite nonwoven substrate was extrusion coated with a bi-layer copolyether ester film using the process conditions and film layers described in Example 1 except that the line speed was adjusted to obtain a film thickness of 23 microns. The properties of the composite fabric are reported below in Table 1.

As can be seen in Table 1, the moisture vapor transmission rate of the composite sheet of Example 3 was greater than that of that of Example 4 where the film was slightly thicker.

It will be apparent to those skilled in the art that modifications and variations can be made in breathable composite sheet material of this invention. The invention in its broader aspects is, therefore, not limited to the specific details or the illustrative examples described above. Thus, it is intended that all matter contained in the foregoing description, drawings and examples shall be interpreted as illustrative and not in a limiting sense.

TABLE 1

| Ex | Film Thickness (μ) | Tensile Strength (N/cm) MD | Tensile Strength (N/cm) CD | Elongation (%) MD | Elongation (%) CD | Basis Wt (g/m$^2$) | MVTR (g/m$^2$/day) | Hydrostatic Head (cm) | Viral Barrier | Peel Strength (N/cm) MD | Peel Strength (N/cm) CD |
|---|---|---|---|---|---|---|---|---|---|---|---|
| 1 | 20 | 7.9 | 1.8 | 23 | 85 | 48.2 | 1320 | 356 | — | 0.77 | 0.70 |
| 2 | 15 | 8.6 | 1.6 | 20 | 60 | 44.8 | 1580 | 277 | — | 0.38 | 0.38 |
| A | 20 | 8.1 | 2.3 | 46 | 97 | 49.5 | 1425 | 76 | — | 0.38 | 0.33 |
| 3 | 20 | 51* | 19* | | | | 1490 | >274 | Pass | 0.46 | 0.42 |
| 4 | 23 | 61* | 26* | | | | 1180 | >389 | Pass | 0.88 | 0.77 |

*Grab tensile

Representative Absorbent Articles

Figure 4:
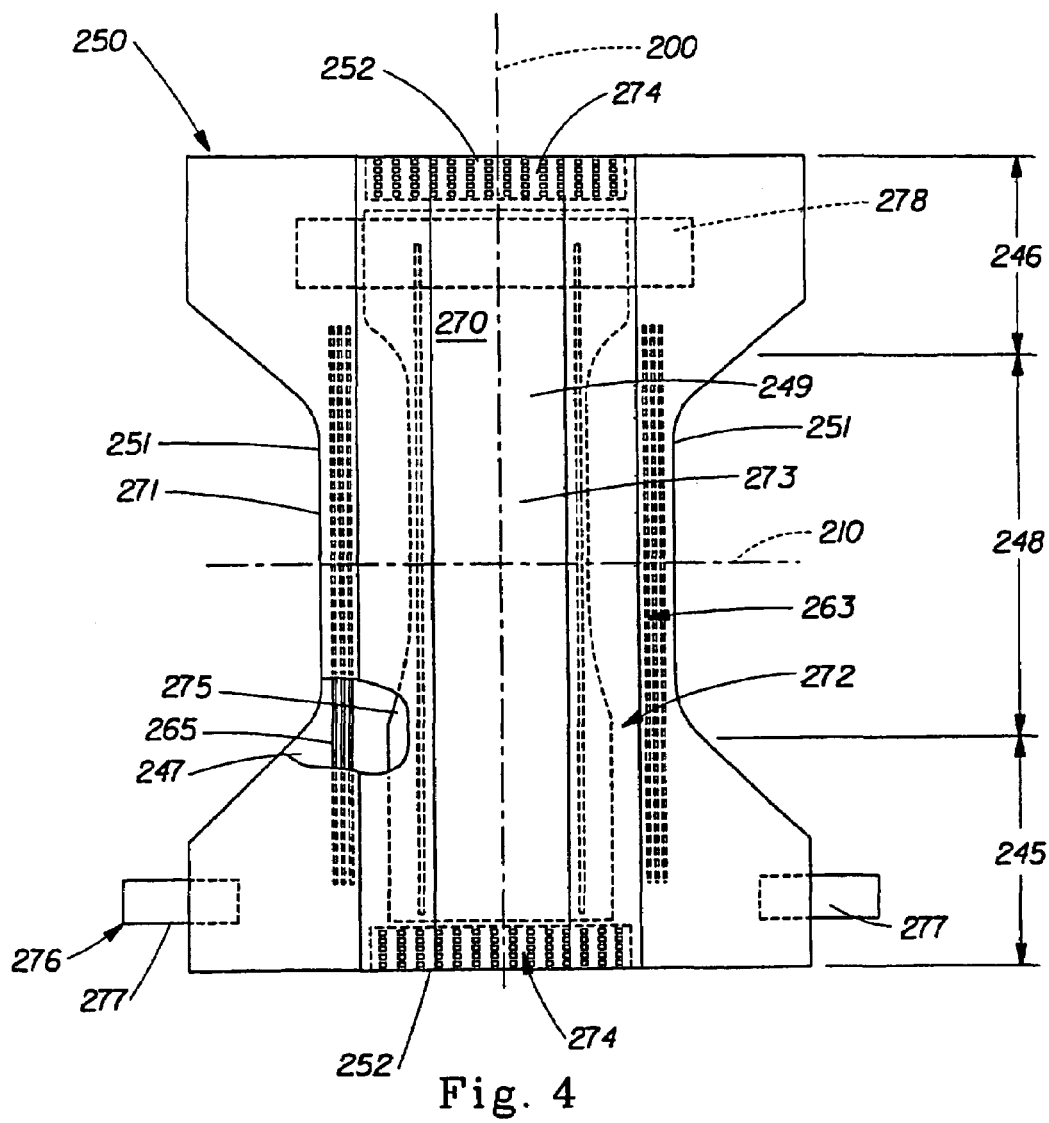
FIG. 4 is a plan view of a disposable diaper embodiment of the present invention having portions cut away to reveal underlying structure, as viewed from the inner surface of the diaper.

A preferred embodiment of an absorbent article incorporating the composite sheet of the present invention is the diaper 250, shown in FIG. 4. As used herein, the term "diaper" refers to an absorbent article generally worn by infants and incontinent persons that is worn about the lower torso of the wearer. FIG. 4 is a plan view of the diaper 250 of the present invention in its flat-out, uncontracted state (i.e., with elastic induced contraction pulled out) with portions of the structure being cut-away to more clearly show the construction of the diaper 250. As shown in FIG. 4, the diaper 250 preferably comprises a containment assembly 270 comprising a topsheet 249; a backsheet 247 joined to the topsheet; and an absorbent core 275 positioned between the topsheet 249 and the backsheet 247. The absorbent core 275 has a pair of opposing longitudinal edges, an inner surface and an outer surface. The diaper preferably further comprises elastic leg features 272; elastic waist features 274; and a fastening system 276 preferably comprising a pair of securement members 277 and a landing member 278.

The diaper 250 is shown in FIG. 4 with the portion of the diaper 250 which faces the wearer, the inner surface 273, facing the viewer. The diaper 250 is shown in FIG. 4 to have an inner surface 273 (facing the viewer in FIG. 4), an outer surface 271 opposed to the inner surface 273, a rear or back waist region 245, a front waist region 246 opposed to the rear waist region 245, a crotch region 248 positioned between the rear waist region 245 and the front waist region 246, and a periphery which is defined by the outer perimeter or edges of the diaper 250 in which the longitudinal or side edges are designated 251 and the end edges are designated 252. The inner surface 273 of the diaper 250 comprises that portion of the diaper 250 which is positioned adjacent to the wearer's body during use (i.e., the inner surface 273 generally is formed by at least a portion of the topsheet 249 and other components joined to the topsheet 249). The outer surface 271 comprises that portion of the diaper 250 which is positioned away from the wearer's body (i.e., the outer surface 271 is generally formed by at least a portion of the backsheet 247 and other components joined to the backsheet 247). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 245 and the front waist region 246 extend from the end edges 252 of the periphery to the crotch region 248.

The diaper 250 also has two centerlines, a longitudinal centerline 200 and a transverse centerline 210. The term "longitudinal", as used herein, refers to a line, axis, or direction in the plane of the diaper 250 that is generally aligned with (e.g. approximately parallel with) a vertical plane which bisects a standing wearer into left and right halves when the diaper 250 is worn. The terms "transverse" and "lateral", as used herein, are interchangeable and refer to a line, axis or direction which lies within the plane of the diaper that is generally perpendicular to the longitudinal direction.

Figure 5:
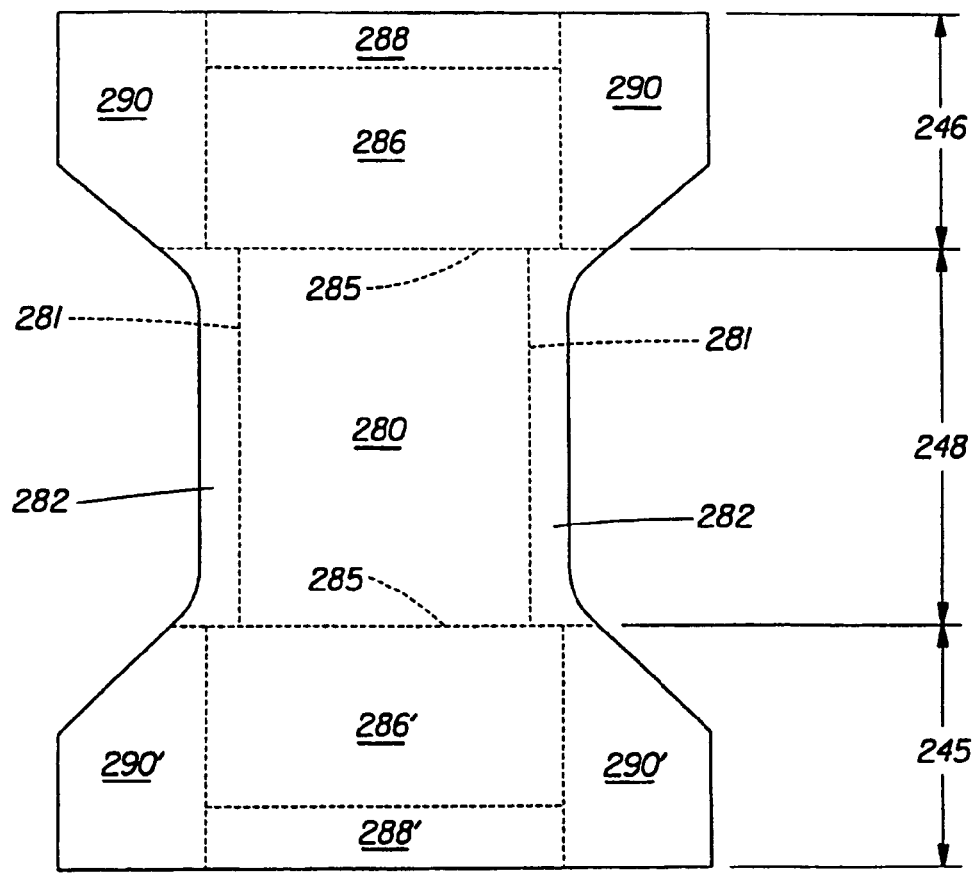
FIG. 5 is a simplified plan view of the disposable diaper of the present invention in its flat uncontracted condition showing the various panels or zones of the diaper.

FIG. 5 shows a simplified plan view of the diaper 250 of FIG. 4 depicting the various panels and their positioning with respect to each other. The term "panel" is used herein to denote an area or element of the diaper. (While a panel is typically a distinct area or element, a panel may coincide (functionally correspond) somewhat with an adjacent panel.) The diaper 250 has a crotch region 248 comprising a main panel 280 and a pair of leg panels 282; a front waist region 246 comprising a central panel comprising a medial panel 286 and a waistband panel 288, and side panels 290; and a rear waist region 245 comprising a central panel comprising a medial panel 286' and a waistband panel 288', and side panels 290'. The main panel 280 is the portion of the diaper 250 from which the other panels emanate. The absorbent core is generally positioned within the main panel 280 since exudates are typically discharged in this region of the diaper although the absorbent core will also likely extend into the medial panels 286 and 286'. A leg panel 282 extends generally laterally outwardly from and along each side edge 281 of the main panel 280. Each leg panel 282 generally forms at least a portion of the elastic leg feature. In the front waist region 246, the medial panel 286 of the central panel extends generally longitudinally outwardly from and along the lateral edge 285 of the main panel 280. The waistband panel 288 extends generally longitudinally outwardly from and along the medial panel 286. The side panels 290 each extend generally laterally outwardly from and along the central panel. In the rear waist region 245, the medial panel 286' of the central panel extends generally longitudinally outwardly from and along the lateral edge 285 of the main panel 280. The waistband panel 288' extends generally longitudinally outwardly from and along the medial panel 286'. The side panels 290' each extend generally laterally outwardly from and along the central panel.

Referring again to FIG. 4, the containment assembly 270 of the diaper 250 is shown as comprising the main body (chassis) of the diaper 250. The containment assembly 270 preferably comprises a topsheet 249, a backsheet 247 and an absorbent core 275 having a pair of opposing longitudinal edges, an inner surface, an outer surface. The inner surface of the absorbent core generally faces the body of the wearer while the outer surface generally faces away from the body of the wearer. When the absorbent article comprises a separate holder and a liner, the containment assembly 270 generally comprises the holder and the liner (i.e., the containment assembly 270 comprises one or more layers of material to define the holder while the liner comprises an absorbent composite such as a topsheet, a backsheet, and an absorbent core.) For unitary absorbent articles, the containment assembly 270 preferably comprises the topsheet 249, the backsheet 247 and the absorbent core 275 of the diaper with other features added to form the composite diaper structure.

FIG. 4 shows a preferred embodiment of the containment assembly 270 in which the topsheet 249 and the backsheet 247 have length and width dimensions generally larger than those of the absorbent core 275. The topsheet 249 and the backsheet 247 extend beyond the edges of the absorbent core 275 to thereby form the periphery of the diaper 250. While the topsheet 249, the backsheet 247, and the absorbent core 275 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; and U.S. Pat. No. 5,385,500 entitled "Absorbent Articles Providing Sustained Dynamic Fit" which issued to LaVon et al., on Oct. 25, 1994; each of which is incorporated herein by reference.

In the embodiment shown in FIG. 4, the backsheet 247 preferably comprises a continuous sheet or layer which defines the front waist region 246, the rear waist region 245, and the crotch region 248. As used herein, the term "layer" does not necessarily limit the element to a single strata of material in that a layer may actually comprise laminates or combinations of sheets or webs of the requisite types of materials. The backsheet 247 has an inner surface and an opposed outer surface. The inner surface is that portion of the backsheet 247 which is positioned adjacent the absorbent core. The outer surface of the backsheet 247 corresponds to the outer surface 271 of the diaper 250. Since the backsheet 247 preferably defines the front waist region 246, the rear waist 245, and the crotch region 248, the backsheet 247 also has corresponding regions and panels as previously defined. (For simplicity, these regions and panels are denoted in the drawings by the same reference numerals as the corresponding diaper regions and panels as shown in FIG. 5.)

In the embodiment shown in FIG. 5, the absorbent core is positioned in the main panel 280, since exudates are typically discharged in this region and extends into the medial panels 286 and 286'. In the embodiment shown in FIG. 5, the absorbent core does not extend into the leg panels 282, the waistband panels 288 and 288', or the side panels 290 and 290'. In other embodiments, the absorbent core may extend into all or some of the leg panels 282, the waistband panels 288 and 288', and the side panels 290 and 290'.

The backsheet 247 of the present invention is that portion of the diaper 250 which is generally positioned away from the wearer's skin and which prevents the exudates absorbed and contained in the absorbent core 275 from wetting articles which contact the diaper 250 such as bedsheets and undergarments. Thus, the backsheet 247 is substantially impervious to fluids (e.g., urine). In addition to being fluid impervious, the backsheet 247 is also highly permeable to moisture vapor. For disposable diapers, moisture vapor permeability has been found to be critical to comfort related performance of absorbent articles. When an absorbent article comprised of non-breathable material is positioned on a wearer, the skin is occluded by the materials making up the absorbent article. This occlusion of the skin prevents escape of moisture vapor or evaporation and the resulting cooling of the occluded area. The resultant increase in perspiration in conjunction with fluid loading raises the relative humidity of air inside of the absorbent article resulting in reduced comfort for the wearer and perceived negative benefits by caregivers. As discussed above, the composite sheet 10 of the present invention has an ideal moisture vapor transmission rate for use as a backsheet in a disposable absorbent article, such as the disposable diaper 250 of FIG. 4. For such an application, the composite sheet 10 is employed with the film layer 12 forming the inner or core-facing portion of the backsheet and the substrate 16 forming the outer or garment-facing portion of the backsheet.

The backsheet 247 comprised of the composite sheet 10 is preferably positioned adjacent the outer surface of the absorbent core 275 and may be joined thereto by any suitable attachment means known in the art for bonding such materials. For example, the backsheet 247 may be secured to the absorbent core 275 by a uniform continuous layer of adhesive, a patterned layer of adhesive, or an array of separate lines, spirals, or spots of adhesive. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Embodiments of the present invention are also contemplated wherein the absorbent core is not joined to the backsheet 247, and/or the topsheet 249 in order to provide greater extensibility in the front waist region 246 and the rear waist region 245.

The absorbent core 275 may be any absorbent member which is generally compressible, conformable, non-irritating to the wearer's skin, and capable of absorbing and retaining fluids such as urine and other certain body exudates. As shown in FIG. 4, the absorbent core 275 has a garment-facing side, a body-facing side, a pair of side edges, and a pair of waist edges. The absorbent core 275 may be manufactured in a wide variety of sizes and shapes (e.g., rectangular, hourglass, "T"-shaped, asymmetric, etc.) and from a wide variety of fluid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 275 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 275 may also be varied to accommodate wearers ranging from infants through adults. However, the total absorbent capacity of the absorbent core 275 should be compatible with the design loading and the intended use of the diaper 250.

One embodiment of the diaper 250 has an asymmetric, modified T-shaped absorbent core 275 having ears in the front waist region but a generally rectangular shape in the rear waist region. Exemplary absorbent structures for use as the absorbent core 275 of the present invention that have achieved wide acceptance and commercial success are described in U.S. Pat. No. 4,610,678 entitled "High-Density Absorbent Structures" issued to Weisman et al. on Sep. 9, 1986; U.S. Pa. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The topsheet 249 is preferably positioned adjacent the inner surface of the absorbent core 275 and is preferably joined thereto and to the backsheet 247 by attachment means (not shown) such as those described above with respect to joining the backsheet 249 to the absorbent core 247. In a preferred embodiment of the present invention, the topsheet 249 and the backsheet 247 are joined directly to each other in the diaper periphery and are indirectly joined together by directly joining them to the absorbent core 275 by any suitable means.

The topsheet 249 is preferably compliant, soft feeling, and non-irritating to the wearer's skin. Further, the topsheet 249 is preferably fluid pervious permitting fluids (e.g., urine) to readily penetrate through its thickness. A suitable topsheet 249 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 249 is preferably made of a hydrophobic material to isolate the wearer's skin from fluids which have passed through the topsheet 249 and are contained in the absorbent core 275 (i.e. to prevent rewet). If the topsheet 249 is made of a hydrophobic material, at least the upper surface of the topsheet 249 is treated to be hydrophilic so that fluids will transfer through the topsheet more rapidly. This diminishes the likelihood that body exudates will flow off the topsheet 249 rather than being drawn through the topsheet 249 and being absorbed by the absorbent core 275. The topsheet 249 can be rendered hydrophilic by treating it with a surfactant. Suitable methods for treating the topsheet 249 with a surfactant include spraying the topsheet 249 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein. As mentioned in the background discussion above, such hydrophilic materials tend to reduce the surface tension of bodily fluids discharged into an absorbent article, which increases the likelihood of liquid seepage if there are pores or pinholes in the backsheet of the article.

An alternative preferred topsheet comprises an apertured formed film. Apertured formed films are preferred for the topsheet because they are pervious to body exudates and yet non-absorbent and have a reduced tendency to allow fluids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

It may also be desirable to provide the disposable absorbent article of the present invention with extensibility or elasticity in all or a portion of the side panels 290. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 290 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 290 further provide more effective application of the diaper 250 since even if the diaperer pulls one side panel 290 farther than the other during the application (asymmetrically), the diaper 250 will "self-adjust" during wear. While the extensible side panels 290 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference.

The extensible side panels, or any other elements of the diaper 250 in which extensibility or elasticity is desirable such as the waistbands may comprise materials that have been "prestrained", or "mechanically prestrained" (i.e., subjected to some degree of localized pattern mechanical stretching to permanently elongate the material), or structural elastic-like webs, as described in U.S. Pat. No. 5,518,801 issued to Chappell et al. on May 21, 1996. The materials may be prestrained using deep embossing techniques as are known in the art. Alternatively, the materials may be prestrained by directing the material through an incremental mechanical stretching system as described in U.S. Pat. No. 5,330,458 issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

The diaper 250 preferably further comprises elastic leg features 272 for providing improved containment of fluids and other body exudates. Each elastic leg feature 272 may comprise several different embodiments for reducing the leakage of body exudates in the leg panels 282 (the elastic leg feature can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free fluids within the garment. Each of these patents are incorporated herein by reference.

While each elastic leg feature 272 may be configured so as to be similar to any of the leg bands, side flaps, barrier cuffs, or elastic cuffs described above, it is preferred that each elastic leg feature 272 comprise at least an inner barrier cuff comprising a barrier flap and a spacing element such as described in the above-referenced U.S. Pat. No. 4,909,803. In a preferred embodiment, the elastic leg feature 272 additionally comprises an elastic gasketing cuff 263 with one or more elastic strands 265, positioned outboard of the barrier cuff such as described in the above-referred U.S. Pat. No. 4,695,278.

The diaper 250 preferably further comprises an elastic waist feature 274 that provides improved fit and containment. The elastic waist feature 274 is that portion or zone of the diaper 250 which is intended to elastically expand and contract to dynamically fit the wearer's waist. The elastic waist feature 274 preferably extends longitudinally outwardly from at least one of the waist edges of the absorbent core 275 and generally forms at least a portion of the end edge of the diaper 250. Disposable diapers are generally constructed so as to have two elasticized waistbands, one positioned in the rear waist region and one positioned in the front waist region, although diapers can be constructed with a single elasticized waistband. Further, while the elastic waist feature 274 or any of its constituent elements can comprise a separate element affixed to the diaper 250, the elastic waist feature 274 may be constructed as an extension of other elements of the diaper such as the backsheet 247 or the topsheet 249, preferably both the backsheet 247 and the topsheet 249. Embodiments are also contemplated wherein the elastic waist feature 274 comprises apertures, as described above, to provide breathability in the waist regions. The elastic waist feature 274 may be constructed in a number of different configurations including those described in U.S. Pat. No. 4,515,595 entitled "Disposable Diapers with Elastically Contractible Waistbandst" issued to Kievit et al. on May 7, 1985 and the above referenced U.S. Pat. No. 5,151,092 issued to Buell; each of these references being incorporated herein by reference.

The diaper 250 also comprises a fastening system 276 which forms a side closure which maintains the rear waist region 245 and the front waist region 246 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994. Each of these patents are incorporated herein by reference.

While a presently preferred embodiment of an absorbent article such as diaper 250 according to the present invention utilizes a composite sheet 10 according to the present invention for substantially the full extent of the backsheet 247, it is to be understood that the absorbent articles are in no way limited to such an embodiment. For example, a backsheet could be constructed from multiple backsheet elements having similar or diverse properties and constructions. One such approach would be to form a backsheet with an external facing surface of a unitary or composite nonwoven layer as a substrate with the film layer comprising only the region of the backsheet where fluid imperviousness is desired.

Moreover, it may also be desirable to reverse the orientation of the layers so as to place the film layer on the external or garment-facing side of the backsheet and the fibrous substrate layer on the internal or absorbent-core-facing side of the backsheet. It may also likewise be desirable to utilize the composite sheet 10 in a dual-sided embodiment wherein both sides of the backsheet would be faced with a fibrous layer. All such variations are contemplated as being within the scope of the present invention. Moreover, depending upon the specific application, the properties provided by the composite sheets of the present invention may also be employed to great advantage in other regions of the absorbent article besides the central portion of the backsheet which overlies the absorbent core structure. For example, the desirable fluid-impervious, moisture-vapor-pervious properties of the composite sheet also provide desirable attributes for peripheral portions of the absorbent article which extend laterally outwardly from the marginal edges of the absorbent core such as the side panels 290, 290' depicted in FIG. 5. Other such "peripheral portions" of the absorbent article for which such attributes may be desirable are in the vicinity of the leg panels 282 including but not limited to various bands, cuffs, and flaps.

Likewise, while much of the foregoing discussion has focused upon the representative absorbent article in the form of diaper 250, it is to be understood that the materials and principles of the present invention are equally applicable to other absorbent articles such as incontinence briefs, incontinence undergarments, diaper holders and liners, feminine hygiene products (sanitary napkins, pantiliners, etc.), training pants, pull-on garments, and the like wherein the materials of the present invention may be employed advantageously. By way of illustration, a backsheet of a sanitary napkin according the present invention could be formed from a composite sheet of the present invention, as could peripheral portions of a sanitary napkin such as wings or side flaps.

After manufacture of the composite sheet 10, and either before or after the sheet's incorporation into an absorbent article, it may be desirable to subject the sheet to a post-formation mechanical process such as creping, straining/activation by rolling with corrugated rolls, or otherwise. One such representative process is described in detail in U.S. Pat. No. 5,518,801 to Chappell et al., the disclosure of which is hereby incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   (a) a topsheet;
   (b) a backsheet formed from a moisture vapor permeable, substantially liquid impermeable composite sheet material, said composite sheet material comprising;
      (i) a first fibrous nonwoven web having a first side and an opposite second side;
      (ii) a second fibrous nonwoven web having a first side and an opposite second side, the first side of said second fibrous nonwoven web abutting the second side of said first fibrous nonwoven web;
      said first and second fibrous nonwoven webs each being powder-bonded webs wherein the fibers of said first and second fibrous webs are bonded to the other fibers of such web by a synthetic adhesive permeating said first and second nonwoven fibrous webs, and wherein the first and second fibrous nonwoven webs are bonded to each other by said adhesive; and
      (iii) a moisture vapor permeable thermoplastic film bonded to the second side of said second fibrous nonwoven web;
      wherein:
         (I) at least 90 weight percent of the fibers in said first fibrous nonwoven web are compatible with said adhesive;
         (II) between 25 and 75 weight percent of the fibers in said second fibrous nonwoven web are compatible with said adhesive and said thermoplastic film;
         (III) between 75 and 25 weight percent of the fibers in said second fibrous nonwoven web are incompatible with said adhesive and said thermoplastic film; and (IV) at least 50 weight percent of the polymer in said thermoplastic film is compatible with said adhesive; and (c) an absorbent core located between said topsheet and said backsheet.

2. The absorbent article of claim 1, wherein the weight of the fibers in said second nonwoven fibrous web is between ¼ and 4 times the weight of the fibers in said first nonwoven fibrous web.

3. The absorbent article of claim 1 wherein said composite sheet exhibits a peel strength of at least 0.1 N/cm, a hydrostatic head of at least 60 cm, and a moisture vapor transmission rate, according to the LYSSY method, of at least 1000 g/m$^2$/24 hr.

4. The absorbent article of claim 1 wherein:
   (a) said adhesive is a polyester polymer or polyester copolymer adhesive;
   (b) said moisture vapor permeable film is comprised of at least about 75% by weight of polymer selected from the group of block copolyether esters, block copolyether amides, copolyether imide esters, polyurethanes, polyvinyl alcohol, and combinations thereof;
   (c) at least 90 weight percent of the fibers in said first fibrous nonwoven web are made of polymer selected from the group of polyester polymers and copolymers;
   (d) between 25 and 75 weight percent of the fibers in said second fibrous nonwoven web are made of polymer selected from the group of polyester polymers and copolymers; and
   (e) between 75 and 25 weight percent of the fibers in said second fibrous nonwoven web are made of polymer selected from the group of polyamides, polyolefins, acrylics, and cotton.

5. The absorbent article of claim 1 wherein said polyester polymers and polyester copolymers in said fibers are selected from the group of poly(ethylene terephthalate), poly(1,3-propylene terephthalate) and copolymers thereof.

6. The absorbent article of claim 1 wherein said moisture vapor permeable film is comprised of at least about 75% by weight of block copolyether esters.

7. The absorbent article of claim 6, wherein said moisture vapor permeable film consists essentially of a copolyether ester elastomer.

8. The absorbent article of claim 1 wherein the composite sheet is substantially free of pinholes, and substantially no liquid passes through the sheet when tested according to the liquid seepage test.

9. The absorbent article of claim 8, wherein said composite sheet prevents passage of microbes when tested according to the ISO 11607 standard for sterile packaging materials.

10. The absorbent article of claim 1 wherein said moisture vapor permeable film has first and second layers, each of said layers being comprised of a different moisture vapor permeable thermoplastic polymer composition.

* * * * *

UNITED STATES PATENT AND TRADEMARK OFFICE
CERTIFICATE OF CORRECTION

| | | |
|---|---|---|
| PATENT NO. | : 7,081,560 B1 | Page 1 of 1 |
| APPLICATION NO. | : 09/980330 | |
| DATED | : July 25, 2006 | |
| INVENTOR(S) | : Hyun Sung Lim and George Joseph Ostapchenko | |

It is certified that error appears in the above-identified patent and that said Letters Patent is hereby corrected as shown below:

Column 19

Line 15, delete "worm" and insert --worn--.

Column 25

Line 16, delete "Waistbandst" and insert --Waistbands--.

Signed and Sealed this

Third Day of July, 2007

JON W. DUDAS
*Director of the United States Patent and Trademark Office*